(12) United States Patent
Manz et al.

(10) Patent No.: US 7,602,281 B2
(45) Date of Patent: Oct. 13, 2009

(54) SYSTEM AND METHOD FOR TACTICAL DISTRIBUTED EVENT WARNING NOTIFICATION FOR INDIVIDUAL ENTITIES, AND COMPUTER PROGRAM PRODUCT THEREFOR

(75) Inventors: Paul C. Manz, Matawan, NJ (US); Fernando J. Maymi, West Point, NY (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 233 days.

(21) Appl. No.: 11/489,802

(22) Filed: Jul. 19, 2006

(65) Prior Publication Data
US 2008/0316021 A1    Dec. 25, 2008

Related U.S. Application Data

(60) Provisional application No. 60/764,388, filed on Jan. 26, 2006.

(51) Int. Cl.
*G08B 26/00* (2006.01)
(52) U.S. Cl. .......... 340/505; 340/506; 340/539.1; 340/3.1; 340/825.36; 340/825.49
(58) Field of Classification Search ............ 340/506, 340/539.1, 3.1, 825.36, 825.49
See application file for complete search history.

(56) References Cited

U.S. PATENT DOCUMENTS

| | | | |
|---|---|---|---|
| 6,018,770 A * | 1/2000 | Little et al. ............ | 709/223 |
| 6,028,514 A | 2/2000 | Lemelson et al. | |
| 6,084,510 A | 7/2000 | Lemelson et al. | |
| 6,832,251 B1 | 12/2004 | Gelvin et al. | |
| 2001/0027389 A1 | 10/2001 | Beverina et al. | |
| 2001/0051996 A1 | 12/2001 | Cooper et al. | |
| 2003/0067542 A1 | 4/2003 | Monroe | |
| 2003/0074672 A1 * | 4/2003 | Daniels ............... | 725/110 |
| 2003/0171939 A1 | 9/2003 | Yagesh et al. | |

(Continued)

*Primary Examiner*—Daryl C Pope
(74) *Attorney, Agent, or Firm*—Michael Zelenka; Stephen J. Harbulak (57) ABSTRACT

An information system, method, and computer program product is provided for the distributed warning of existing or developing significant events and/or threats to users carrying a user warning and positioning device, while reporting the location of all user's carrying the user warning and positioning devices of the system to existing command and control systems. The present invention's future event warning capabilities permit those same users to be warned of impending events in enough time for the users to take positive actions in response to these events and/or address those events. The system of the present invention includes a pager-like user warning and positioning device, worn by or carried by the individual user, or mounted in a vehicle or vessel, having a geographical positioning means therein, which periodically transmits the geographical location of the individual user, vehicle or vessel, and listens for warning/notification event messages transmitted by a network bridge or situational awareness workstation (central processing means). When an event/threat warning is received by the user warning and positioning device, the pager-like user warning and positioning alerts the user via indicia relative to the event/situation, including audible spoken warnings and instructions on how to react, and may retransmit the event/threat warning to other user warning and positioning devices in the network, provided the threat has not occurred and the event/threat warning has not been previously relayed.

21 Claims, 3 Drawing Sheets

U.S. PATENT DOCUMENTS

| | | |
|---|---|---|
| 2003/0204748 A1 | 10/2003 | Chiu |
| 2004/0070515 A1 | 4/2004 | Burkley et al. |
| 2004/0100379 A1 | 5/2004 | Boman et al. |
| 2004/0198254 A1 | 10/2004 | Mizui et al. |
| 2004/0252049 A1 | 12/2004 | Vantalon et al. |
| 2005/0003812 A1* | 1/2005 | Gladwin et al. .......... 455/426.1 |
| 2005/0078647 A1* | 4/2005 | Meier et al. ................. 370/338 |
| 2005/0108582 A1* | 5/2005 | Fung .......................... 713/300 |
| 2005/0143013 A1 | 6/2005 | Jha |
| 2005/0197775 A1* | 9/2005 | Smith ............................ 702/3 |
| 2005/0219044 A1 | 10/2005 | Douglass et al. ............ 340/506 |
| 2005/0240378 A1* | 10/2005 | Smith et al. ................. 702/188 |
| 2005/0243867 A1 | 11/2005 | Petite |
| 2005/0272368 A1 | 12/2005 | Langsenkamp et al. |
| 2006/0141940 A1* | 6/2006 | Bloom et al. ................. 455/73 |
| 2006/0168592 A1 | 7/2006 | Andrews et al. ............ 719/318 |
| 2006/0187017 A1 | 8/2006 | Kulesz et al. ............... 340/506 |
| 2007/0115116 A1* | 5/2007 | Zabek .................... 340/539.22 |

* cited by examiner

SYSTEM AND METHOD FOR TACTICAL DISTRIBUTED EVENT WARNING NOTIFICATION FOR INDIVIDUAL ENTITIES, AND COMPUTER PROGRAM PRODUCT THEREFOR

CROSS REFERENCE TO RELATED APPLICATION

This application claims the benefit of U.S. Provisional Patent Application Ser. No. 60/764,388, entitled "System and Method for Tactical Distributed Event Warning/Notification for Individual Entities" and filed Jan. 26, 2006, which is fully incorporated herein by reference herein.

STATEMENT OF GOVERNMENT INTEREST

The invention described herein may be manufactured, used, imported, sold, and licensed by or for the Government of the United States of America without the payment or any royalty thereon or therefor.

FIELD OF THE INVENTION

The present invention relates to the field of communications notification and warning systems, and more particularly, to a network information system that combines hardware components and a corresponding computer software system to provide a distributed system and method for real-time event warning/notification to numerous individual entities across dispersed locations via one or more central event/threat receiving stations, one or more network bridges, and one or more user warning and positioning devices.

BACKGROUND OF THE INVENTION

One of the salient features of today's modern organizations on a global, national, regional and local level is the ability to leverage information technology to command and control systems in real or near-real time. Advances in the technologies that integrate sensor and communications systems, for instance, facilitate determination of the precise location of mobile vehicles. Also, a plurality of modem information systems permit such location determination, including space, airborne, terrestrial and marine-based command and control systems.

Every vehicle equipped with such a command and control system is able to determine the location using global positioning system (GPS) technology, and then report that vehicle's information to higher command structures/systems using secure wireless linkages. Vehicles equipped with command and control systems also receive a variety of messages from higher command structures/systems, including the known locations of other related vehicles and other unknown or suspected locations of non-related vehicles. Command and control systems also allow vehicles to send and receive warning messages and in turn permit, for instance, the alerting of related vehicles about such significant events whether developing or in progress.

Though command and control systems warning messages are often manually generated, there are other information systems in use today, such as weather and tsunami stations, that automatically generate threat warning messages without human intervention. One of the military systems that automatically generates a threat warning message is the AN/TPQ-36 Firefinder Counter-fire Radar, which is able to detect projectiles in flight, compute their predicted points of origin and predicted points of impact, and automatically broadcast this information to other systems. The above described system still leaves the most numerous and vulnerable assets, humans, exposed to threats. Thus, there is a need to significantly enhance survivability.

Accordingly, there is a need for a network information system that allows command organizations/structures to know the location in real time of all their remote human assets, such as dismounted soldiers, emergency responders, remote construction crews, etc., as well as warn those assets whenever an event, such as a threat, exists or is inbound. These warnings must be expeditiously distributed, received, and processed to permit sufficient time for potentially affected human assets to alter their protective posture and/or take positive actions in response to the predicted event. In the past, this quick response time has not been achieved in practice. This is understandable when considering the vast number of end systems, and resulting costs required to equip every remote human asset in a field of operations.

Accordingly, there is a need for a system that enables training, simulation, and rehearsal capabilities, along with real-time use by organizations, first responders, public safety, emergency management personnel, etc. for providing warning of harmful events, such as natural disasters, medical emergencies, military threats, homeland security events, and natural disaster incidents. In addition, there is a need for remotely located individuals, such as skiers, hikers, etc. to be provided with warning of harmful events, such as sudden violent weather changes, avalanches, and natural disasters. Further, there is a need for remotely located vehicles and vessels to be provided with a warning of potentially harmful events, such as, for example, violent ocean conditions, sea state changes, and tidal waves.

It is, therefore, an object of the present invention to provide a networked information system and method that combines a plurality of components to effectively distribute a real-time event warning/notification to many individual entities across dispersed locations, as well as a computer program product therefor. These individual entities, in turn, can then determine, at the individual point, whether or not these predicted events pertain to their locales, and react accordingly.

It is another object of the present invention to enable the networked information system to monitor other connected information systems for externally and internally generated event warning/notification messages.

It is yet another object of the present invention to transmit event warning/notification messages on a secure wireless network whenever these are received.

It is another object of the present invention to retransmit received event warning/notification messages to other user warning devices that may not have received the original message.

It is a further object of the present invention to provide a tailored event warning/notification to a user of the networked information system, method and computer program product of the present invention, based on message and user-defined setup parameters.

Still a further object of the present invention is to track the location of each equipped organization, individual human asset and/or vehicle, and periodically report this information to designated command and control organizations/structures, whether space-based, airborne, terrestrial and/or marine-based, using standard or customized messaging formats.

Another object of the present invention is to enable the warning of each equipped organization, individual human asset, vehicle, or other entity every time a significant event is predicted to occur or impact within a given distance from the individual user's location. In doing so, it is desirable that the distance parameter be kept to a minimum, to preclude false positives, but also account for an expected event radius or area as well as for errors in determining the location of the user, and of the predicted point of event or impact.

It is another object of the present invention to provide a secure network system, by using encrypted communications. However, the end system itself should not compromise friendly forces, even when captured intact by an opponent. This means that the information contained in the devices carried by individual assets should be minimal, and of extremely limited utility to an adversary, in the case of a military or confidential application.

Furthermore, it is an object of the present invention to incorporate mechanisms that allow lost or captured devices to be selectively excluded from participating in the network.

It is still another object of the present invention to permit assets/users to carry an unobtrusive user warning notification device that is of minimal size. It is also an object of the present invention that the system user warning device be capable of operating for extended periods of times, on the order of weeks and months, in a tactical environment, with no required user interaction.

It is a further object of the present invention that the networked information system, method and computer program product of the present invention be applicable to training, simulation and rehearsal, along with real-time use by organizations, such as first responders, public safety, emergency management personnel, and provide warning of harmful events, such as emergency response, homeland security, natural disaster incidents. In addition, it is an object of the present invention that the system, method and computer program product be applicable to remotely located individuals, such as skiers, hikers, etc., to be provided warning of harmful events, such as sudden violent weather changes, avalanches, natural disasters, etc.

Further, it is an object of the present invention that same be applicable to remotely located vehicles and vessels, so as to provide warning of harmful events, such as violent ocean conditions/sea state changes/tidal waves, for example.

It is also an object of the present invention, in order to overcome the difficulties discussed above, to provide a system and software program product for use in such a system, to automatically facilitate the real-time user warning notification to many individual entities across dispersed locations.

These and other objects in advantages of this invention will become apparent when considered in light of the following description when taken together with the accompanying drawings.

Accordingly, the present invention provides a robust, versatile and cost-effective solution for event warning/notification for individual entities. Unlike other notification approaches, this method allows for remote and virtually instantaneous, distributed notification of future events or threats.

SUMMARY OF THE INVENTION

The present invention has been made to solve the problems associated with the prior art inability to cost-effectively provide real-time warning notification to numerous remotely located human assets (users), as described above. In order to achieve the objects of the present invention, as discussed above, the present inventors have earnestly endeavored to create a network information system, method, and computer program product to use in the network information system, to effectively distribute to numerous individuals over a dispersed area, event warning messages in a timely fashion.

In particular, in a first embodiment of the present invention, a network event warning system enabling distribution of event warning messages to one or more individual entities within the network information system is provided comprising:

(a) one or more situational awareness workstation and threat warning gateways capable of receiving event warnings from linked and/or remote sensors, and/or other externally generated event warning messages, each of said situation awareness workstation and threat warning gateway comprising:

a gateway wireless communications means capable of receiving and transmitting data; and situational awareness workstation computing means in communication with the situational awareness workstation and threat warning gateway and wireless communication means, said situational awareness workstation computing means;

(b) one or more network bridges in communication with the situational awareness workstation and threat warning gateway, each network bridge defining a local node, said network bridges providing a communications interface between individual user warning and positioning devices and the situational awareness workstation and threat warning gateway, each of said network bridges comprising:

(i) a network bridge wireless communications means capable of receiving and transmitting data; and (ii) network bridge computer processing means in communication with the network bridge and network wireless communications means, individual user warning devices, sensors, and command and control systems;

(c) one or more user warning and positioning devices, each user warning and position device defining an individual node, each of said devices comprising:

(i) a warning device computer processing means;

(ii) a ground positioning system (GPS) means capable of calculating the location of the user warning device;

(iii) a wireless communications means; and (iv) one or more sensory notification means;

(d) network situational awareness workstation application program code embodied on a computer readable medium for execution on the situational awareness workstation and threat gateway computer processing means capable of authenticating event warning messages, processing and analyzing the event warning messages via an event prediction determination process to produce predicted future event warning messages, and distributing future event warning messages to the network bridges comprising:

(i) application program code operable to decode and authenticate a valid event warning message, input directly or indirectly into the situational awareness workstation and threat warning gateway, by verifying the digital signature of the event warning message;

(ii) application program code operable to input and authenticate event warning message into an event prediction determination process, thereby analyzing the event warning message to predict a corresponding future event with associated relevant information including predicted event type, location, area impacted, start time, and duration;

(iii) application program code operable to distribute the predicted future event and associated relevant information to all network bridges within the information network, without regard to whether a specific local or individual node will be affected by the predicted future event;

(iv) application program code operable to convert the format of the predicted future event information, in terms of electronic format and content, to alternative electronic formats, before distribution;

(e) bridge application program code embodied on a computer readable medium for execution on the network bridge computer processing means for processing event warning messages received from the situational awareness workstation and threat warning gateway, and other external sources, and distributing an authenticated event warning message of an event to occur in the future, said bridge application program code comprising:

(i) application program code operable to automatically verify the authenticity of event warning messages reporting an event to occur in the future, by examining its digital signature, so as to produce either an invalid or valid event warning message;

(ii) application program code operable to input a valid event warning message into an event prediction process, wherein the predicted time of the event is compared with the local time, to determine whether the event will occur at some future time;

(iii) application program code operable to automatically compare the locale to be affected by an authenticated event warning message of an event to occur in the future within the locale of the local node, to determine the affected area;

(iv) application program code operable to send notification to all user warning and positioning devices within the affected area of an authenticated event warning message of an event predicted to occur in the future;

(v) application program code operable to relay the event warning message to other local and individual nodes not in the area of the predicted strike warning message;

(vi) application program code operable to log off and discard all invalid and elapsed event warning messages;

(vii) application program code operable to input and translate authenticated event warning messages from individual user warning and positioning devices into other message formats utilized by other different command and control systems;

(viii) application program code operable to filtering event warning messages that should not be sent from one network to the other;

(ix) application program code operable to track the status of user warning and positioning devices with which the network bridge is in communication with;

(x) application program code operable to enable the network bridges to communicate with sensors, individual user warning and positioning devices, and command and control systems, using different networks and protocols;

(xi) application program code operable to issue keys acting as the root certificate authority for all nodes in the network, thereby permitting the network bridges and user warning and positioning devices to authenticate each other;

(f) user warning and positioning device application program code embodied on a computer-readable medium for execution on the user warning device computer processing means in conjunction with the bridge application program code and the situational awareness workstation program code, said user warning device application program code being capable of decoding messages, validating and analyzing event warning messages, and then issuing a notification of an event predicted to occur in the future in the locale of the user warning device, said user warning device application program code comprising:

(i) application program code operable to authenticate event warning messages by verifying the digital signature of the event warning messages;

(ii) application program code operable to decoding incoming coded messages;

(iii) application program code operable to query a local cache of messages to determine whether an event warning message has already been relayed;

(iv) application program code operable to relay event warning messages concerning an event that has not as yet happened and has not as yet been relayed;

(v) application program code operable to compare the time of the predicted event to the local time, to determine whether the predicted event will occur at some future time and, if it will, authenticate the message;

(vi) application program code operable to compare the locale to be affected by the predicted future event with the locale of the individual node;

(vii) application program code operable to notify local nodes within the affected area of the predicted future event, and activating user warning devices based upon the time remaining until the predicted event; and (viii) application program code operable to activate one or more of the sensory notification means in the user warning devices when a valid event warning message is received.

In a second embodiment of the present invention, the network event warning system of the first embodiment is provided, wherein the bridge application program code further comprises:

application program code operable to selectively disable or alter individual user warning devices that appear to have been compromised or lost.

In a third embodiment of the present invention, the network event warning system of the first embodiment is provided, wherein the bridge application program code further comprises:

application program code operable to reconfigure any parameters in the individual user warning devices and application program code therein.

In a fourth embodiment of the present invention, the network event warning system of the first embodiment is provided, wherein the bridge application program code further comprises:

application program code operable to interface one or more of the network bridges with an optional laptop computer running on an operating system.

In a fifth embodiment of the present invention, the network event warning system of the first embodiment is provided, wherein the bridge application program code further comprises:

application program code operable to revoke the certificate of a user's warning device.

In a sixth embodiment of the present invention, the network event warning system of the first embodiment above is provided, wherein the user warning and positioning device application program code further comprises:

application program code operable to convert event warning messages to human voice warnings, said human voice warnings comprising instructions on what subsequent action to take.

In a seventh embodiment of the present invention, the network event warning system of the first embodiment is provided, wherein the user warning and positioning device application program code further comprises:

application program code operable to encrypt outgoing messages.

In an eighth embodiment of the present invention, the network event warning system of the first embodiment is provided, wherein the user warning and positioning device application program code further comprises:

application program code operable to utilize spread-spectrum technology to prevent basic triangulation efforts to locate the user warning and positioning device.

In a ninth embodiment of the present invention, the network event warning system of the first embodiment is provided, wherein the user warning and positioning devices are capable of communicating over wired or wireless systems to the network bridges and other user warning devices.

In a tenth embodiment of the present invention, the network event warning system of the first embodiment is provided, wherein the user warning and positioning device application program code further comprises:

application program code operable to reconfigure the files stored in the user warning device.

In an eleventh embodiment of the present invention, the network event warning system of the first embodiment is provided, wherein the bridge application program code further comprises:

application program code operable to connect user warning and positioning devices to command and control systems and sensor systems.

In a twelfth embodiment of the present invention, a computer program product for tactical distributed event warning over a network event warning system is provided, comprising:

(a) network situational awareness workstation application program code embodied on a computer readable medium for execution on a central computer processing means capable of authenticating received event warning messages, processing and analyzing the event warning messages via an event prediction determination process to produce predicted future event warning messages, and distributing future event warning messages to network bridges comprising:

(i) application program code operable to decode and authenticate a valid event warning message, input directly or indirectly into the central computer processing means, by verifying the digital signature of the event warning message;

(ii) application program code operable to input and authenticate event warning messages into an event prediction determination process, thereby analyzing the event warning message to predict a corresponding future event with associated relevant information including predicted event type, location, area impacted, start time, and duration;

(iii) application program code operable to distribute the predicted future event and associated relevant information to all network bridges within the network, without regard to whether a specific local or individual node will be affected by the predicted future event;

(iv) application program code operable to convert the format of the predicted future event information, in terms of electronic format and content, to alternative electronic formats, before distribution;

(b) bridge application program code embodied on a computer readable medium for execution on a network bridge computer processing means for processing event warning messages received from the central computer processing means, and other external sources, and distributing an authenticated event warning message of an event to occur in the future, said bridge application program code comprising:

(i) application program code operable to automatically verify the authenticity of event warning messages reporting an event to occur in the future, by examining its digital signature, so as to produce either an invalid or valid event warning message;

(ii) application program code operable to input a valid event warning message into an event prediction process, wherein the predicted time of the event is compared with the local time, to determine whether the event will occur at some future time;

(iii) application program code operable to automatically compare the locale to be affected by an authenticated event warning message of an event to occur in the future within the locale of the local node, to determine the affected area;

(iv) application program code operable to send notification to all user warning and positioning devices (individual nodes) of an authenticated event warning message of an event predicted to occur in the future;

(v) application program code operable to relay the event warning message to other local and individual nodes not in the area of the predicted strike warning message;

(vi) application program code operable to log off and discard all invalid and elapsed event warning messages;

(vii) application program code operable to input and translate authenticated event warning messages from individual user warning and positioning devices into other message formats utilized by other different command and control systems;

(viii) application program code operable to filtering event warning messages that should not be sent from one network to the other;

(ix) application program code operable to track the status of user warning and positioning devices with which the network bridge is in communication with;

(x) application program code operable to enable the network bridges to communicate with sensors, individual user warning and positioning devices, and command and control systems, using different networks and protocols;

(xi) application program code operable to issue keys acting as the root certificate authority for all nodes in the network, thereby permitting the network bridges and user warning and positioning devices to authenticate each other;

(c) user warning and positioning device application program code embodied on a computer-readable medium for execution on a user warning device computer processing means in conjunction with the bridge application program code and the situational awareness workstation program code, said user warning device application program code being capable of decoding messages, validating and analyzing event warning messages, and then issuing a notification of an event predicted to occur in the future in the locale of the user warning device, said user warning device application program code comprising:
- (i) application program code operable to authenticate event warning messages by verifying the digital signature of the event warning messages;
- (ii) application program code operable to decoding incoming coded messages;
- (iii) application program code operable to query a local cache of messages to determine whether an event warning message has already been relayed;
- (iv) application program code operable to relay event warning messages concerning an event that has not as yet happened and has not as yet been relayed;
- (v) application program code operable to compare the time of the predicted event to the local time, to determine whether the predicted event will occur at some future time and, if it will, authenticate the message;
- (vi) application program code operable to compare the locale to be affected by the predicted future event with the locale of the individual node;
- (vii) application program code operable to notify local nodes within the affected area of the predicted future event, and activating user warning and positioning devices based upon the time remaining until the predicted event; and
- (viii) application program code operable to activate one or more sensory notification means in the user warning and positioning devices when a valid event warning message is received.

In a thirteenth embodiment of the present invention, the computer program product of the twelfth embodiment above is provided, wherein the network bridge application program code further comprises:

application program code operable to selectively disable or alter individual user warning and positioning devices that appear to have been compromised or lost.

In a fourteenth embodiment of the present invention, the computer program product of the twelfth embodiment above is provided, wherein the network bridge application program code further comprises:

application program code operable to reconfigure any parameters in the individual user warning and positioning devices and application program code therein.

In a fifteenth embodiment of the present invention, the computer program product of the twelfth embodiment above is provided, wherein the network bridge application program code further comprises:

application program code operable to interface one or more network bridges with an optional laptop computer running on a conventional operating system.

In a sixteenth embodiment of the present invention, the computer program product of the twelfth embodiment is provided, wherein the network bridge application program code further comprises:

application program code operable to revoke the certificate of a user warning and positioning device.

In a seventeenth embodiment of the present invention, a method for receiving and tactically distributing event warnings is provided, said method comprising the steps of:
- (1) electronically receiving an event warning message, having a digital signature, at a situational awareness workstation;
- (2) examining the digital signature of the event warning message to authenticate the event warning message;
- (3) decoding the authenticated event warning message into a readable format;
- (4) analyzing the authenticated event warning message so as to generate corresponding predicted event and associated relevant information, said predicted event and associated relevant information including event type, event location, area impacted, event start time, and event duration, so as to define an event warning message;
- (5) converting the event warning message to an electronic format and content readable by a network bridge (local node) and a user warning and positioning device (individual node);
- (6) distributing the event warning message by transmission of same from the situational awareness workstation to one or more network bridges, without regard to whether a specific local or individual node will be affected by the predicted event;
- (7) receipt of the event warning message in one or more network bridges, and verifying, in the network bridges, the validity of the event warning message received from the situational awareness workstation, so as to authenticate same;
- (8) comparing, in the network bridges, the predicted time of the predicted event in the authenticated event warning message with the local time, to determine whether the event has already occurred, and if the predicted event has not occurred, generate a future authenticated event warning message;
- (9) filtering out event warning messages, at the network bridges, that should not be sent from one network to another, due to lack of validity or authenticity;
- (10) translating the future authenticated event warning messages at the network bridge into other message formats utilized by other different command and control systems and user warning and positioning devices;
- (11) issuing, at the network bridges, keys acting as the root certificate authority for all nodes in the network information system, permitting the network bridges and user warning and positioning devices to authenticate each other;
- (12) tracking the status of user warning and positioning devices in communication with the network bridge, to determine active or inactive status thereof;
- (13) distributing the valid, converted and authenticated event warning message from the network bridges to one or more active user warning and positioning devices;
- (14) receiving the valid, converted and authenticated event warning message at the user warning and positioning devices,
- (15) examining, in the user warning and positioning devices, the digital signature of the incoming event warning message to verify its authenticity;
- (16) discarding all invalid and elapsed warning messages at the user warning and positioning devices;
- (17) comparing the locale to be affected by the valid and authenticated event warning message with the locale of the individual node;
- (18) comparing in the user warning devices the time of the predicted event or threat in the strike warning message to the local time to determine whether the event will occur at some future time and, if it will, authenticating the message;
- (19) decoding, in the user warning and positioning devices, incoming coded event warning messages;

(20) activating one or more notification mechanisms in the user warning and positioning devices, including sensory mechanisms, a user notification concerning the received event warning message.

In an eighteenth embodiment of the present invention, the method for receiving and tactically distributing event warnings of the seventeenth embodiment above is provided, further comprising the step of establishing and maintaining communication between the bridge, sensors, user warning devices and command and control systems using different networks and protocols;

In a nineteenth embodiment of the present invention, the method for receiving and tactically distributing event warnings of the seventeenth embodiment above is provided, further comprising:

(21) sending a query from the user warning and positioning devices to a local cache of messages to determine whether the event warning message has already been relayed; and (22) relaying, from the user warning and positioning devices to other nodes in the network information system, the event warning message concerning an event that has not as yet happened and has not as yet been relayed;

In a twentieth embodiment of the present invention, the method for receiving and tactically distributing event warnings of the seventeenth embodiment above is provided, further comprising converting valid event warning messages to human voice warnings with instructions on what subsequent action to take.

In a twenty first embodiment of the present invention, the method for receiving and tactically distributing event warnings of the seventeenth embodiment above is provided, further comprising sending messages from one or more of the network bridges to one or more of user warning and positioning devices, to either alter, reconfigure, or disable one or more of the user warning and positioning devices.

BRIEF DESCRIPTION OF THE DRAWINGS

The accompanying drawings, which are included to provide further understanding of the present invention, and are incorporated in and constitute a part of the specification, illustrating samples of the present invention and together with the description serve to explain the principles of the present invention. The invention will now be described further with reference to the accompanying drawing in which.

DETAILED DESCRIPTION OF THE PREFERRED EMBODIMENTS

The following section describes various preferred embodiments of the present invention, while exemplifying the distributed event warning/notification system, method, and computer program software of the present invention.

The present invention applies engineering design principles to improve commercial products and military applications for situational awareness and event warning. The present invention is a networked information system that combines hardware components, wireless technologies, and computer software programs to provide a distributed system and method for real-time event warning/notification to many individual entities across dispersed locations.

These entities, in turn, determine whether or not these events pertain to their locales and react accordingly. For instance, if the system is notified that an artillery shell is in the air and will strike a certain point at a certain time, this message will be distributed to all nodes within the system (i.e., all user warning and positioning devices), allowing the nodes within the danger radius to alert their users while all other nodes remain silent. The present invention supports a plurality of network types, e.g., radio, local area networks, etc.

The present invention's system architecture satisfies the present invention's objectives by determining, at the user location, whether a user, such as a public safety professional or soldier is inside a predicted future event area. This system and method achieves same by comparing the location of an individual user at the time of receipt of the future event warning at the user warning and positioning device with each known event or threat area to determine whether or not said user must be warned at that time, or at a later time up through the predicted future time of the event as the user changes geographic locations. This is the most computationally intensive calculation required to satisfy the system and method objectives, as errors in this calculation can either erode trust in the system or result in injury or death, or both, of the user. Accordingly, the present invention's architecture permits the ongoing computation of user locations and threat areas at the end user warning and positioning devices from the time of receipt of the future event warning message at the user warning and positioning device up to the predicted future event time.

The present invention further provides a robust solution in the case of the loss, compromise or incapacitation of a computational node, e.g., the user warning device, by affecting only the individual user, such as a public safety professional or soldier, for example. Specifically, according to the present invention, network bridges are utilized to connect the user warning and positioning devices to the command and control and sensor systems, wherein the user warning and positioning devices are not affiliated with a specific network bridge. Instead, each user warning and positioning device is able to exchange messages with any other system component, whether another user warning and positioning device or a network bridge. The present invention is advantageous in that it increases the robustness of the ability to provide warnings within an event area or structure, such as a building, since each node is often multi-homed.

Figure 1:
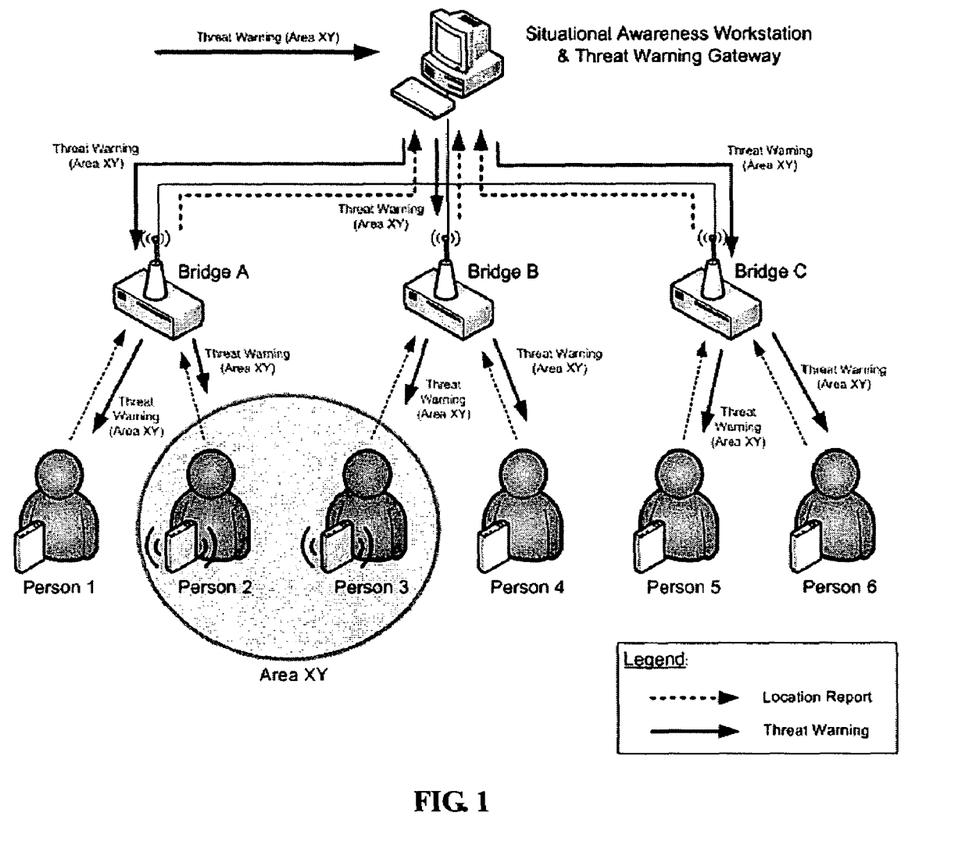
FIG. 1 is a perspective view of the distributed event warning/notification system for individual entities of the present invention, illustrating the flow of information to the situational awareness work station and threat warning gateway, the affiliated network bridges, and all individual user warning and positioning devices of the present invention.
Figure 2:
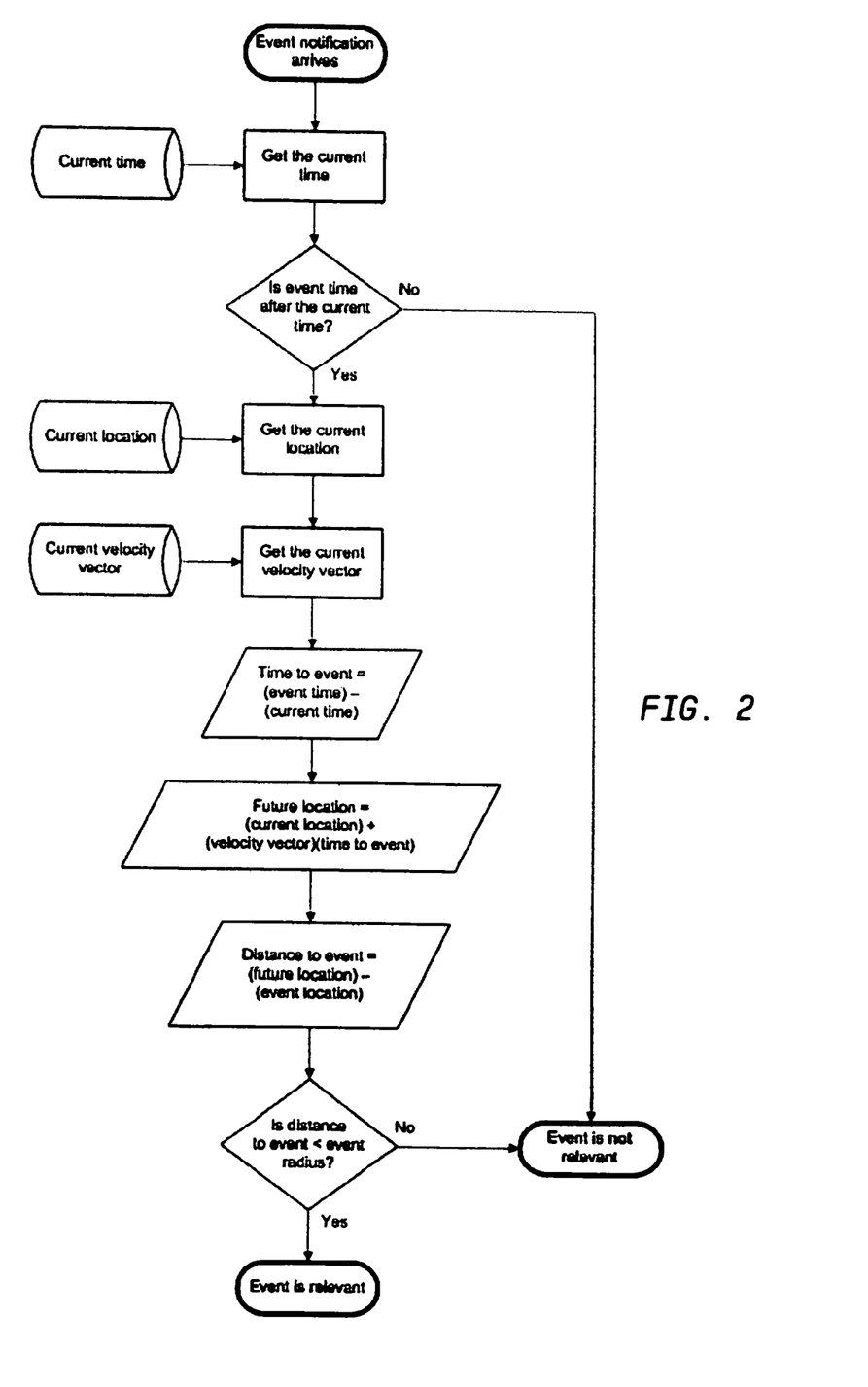
FIG. 2 is a flow diagram, illustrating the functions and steps undertaken by the computer program product of the present invention in receiving and processing future event warning messages at the situational awareness workstation and threat warning gateway, to determine whether the event is relevant and in condition for transmission to the local and individual nodes.
Figure 3:
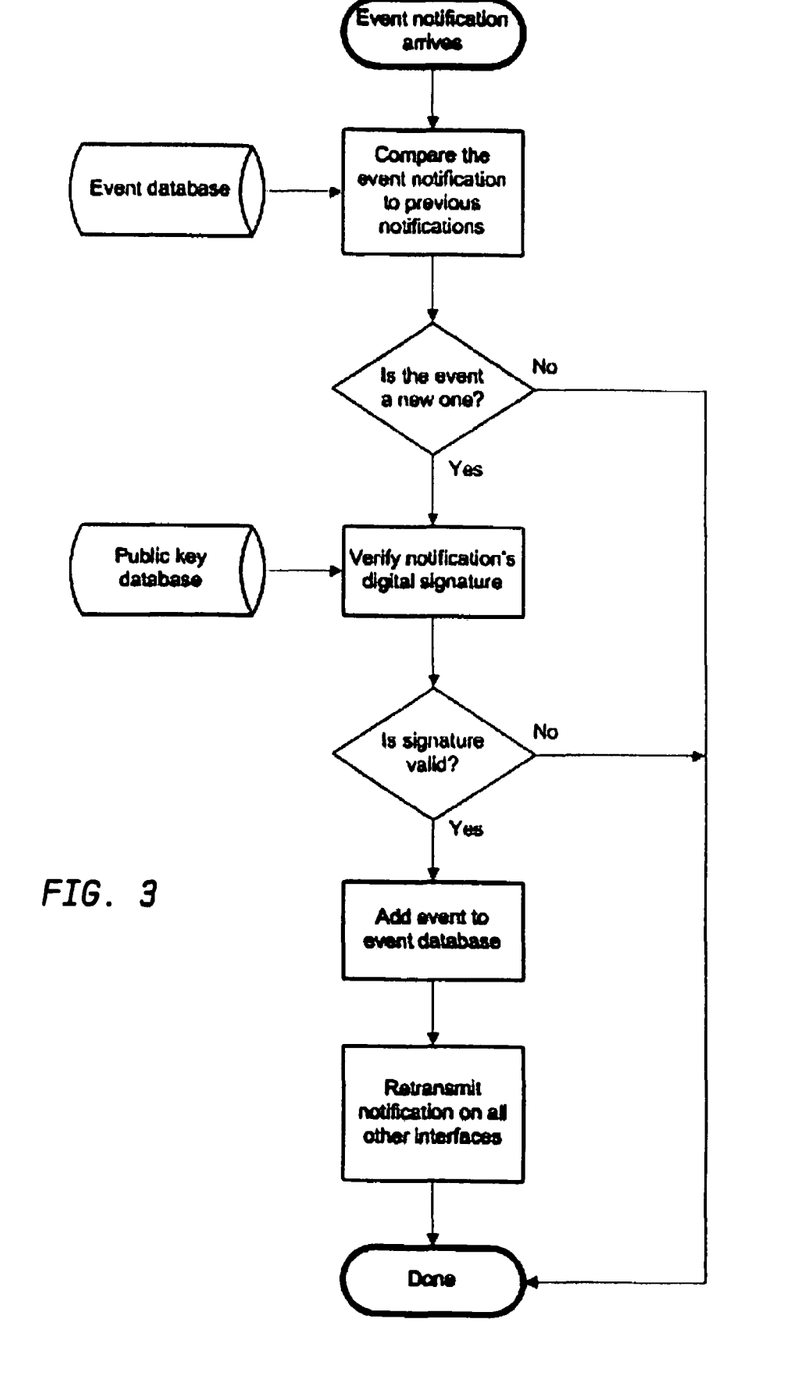
FIG. 3 is a flow diagram, illustrating the decision-making process carried out by the network bridge computer program product of the present invention in determining whether to relay an event warning message received from the situational awareness workstation and threat warning gateways.

Accordingly, FIG. 1 illustrates the distributed warning/notification method and system of the present invention. One or more situational awareness workstation and threat warning gateways (hereinafter "gateways") is established that provides the principle data management in communication with network bridge structures (A, B, C, etc.), which in turn are in communication with user warning and positioning devices on assets (1, 2, 3, 4, 5, 6, etc.), being humans, in this example. Event warning information concerning an event locale, e.g., area XY, is delivered to the gateways. Subsequently, an event warning message is communicated to network bridges A, B and C, and in turn communicated to the user warning and positioning devices in communication therewith. Location (position) information of the assets (users) is generated in the user warning and positioning devices, via a geographical positioning means (GPS) located therein, and periodically communicated to network bridges, e.g., A, B, C, etc., via wireless transmission means.

The location information received from the individual user warning and positioning devices is then communicated from the network bridges to the gateways. For example, as shown in FIG. 1, for Area XY, there is an event warning message that is communicated to the gateway and, subsequently, location and event warning/notification information, in the form of an event warning message, is communicated between individual user warning and positioning devices (individual nodes), the network bridges (local nodes) and the gateway. Moreover, event and asset location information is communicated not only to those assets (individual nodes) within the affected or threat area, but also to and between assets not in the affected or threat area. Thus, threat and location information is communicated to all associated user warning and positioning devices in the system.

The present invention's system includes three types of nodes: the gateways (central nodes), the network bridge devices (local nodes), and user warning and positioning devices (individual nodes), e.g., pager-sized modularized user warning and positioning devices, as illustrated in FIG. 1. The network bridge devices communicate on at least two separate networks. Most commonly, one of these networks is the network over which the pager-size user warning and positioning devices communicate. The other network(s) allows the system to receive externally-generated event warning/notification messages.

The pager-sized user warning and positioning devices communicate wirelessly with the network bridge devices that receive alerts from the situational awareness workstation and threat warning gateway, other network bridge devices, other user warning and positioning devices and/or other information systems communicating over a wired or wireless network. According to the present invention, although a fixed infrastructure may be utilized, there is no need for a fixed infrastructure. Given the need for user warning and positioning devices to communicate with each other, as well as with any network bridges within range, the wireless communications subsystem must support a large number of nodes (i.e., a large number of network bridges and user warning and positioning devices) operating simultaneously within a broadcast environment.

Furthermore, since the system of the present invention can be deployed to hundreds of assets, e.g., soldiers in a theater of operation, emergency response personnel, etc., the wireless communications subsystem must also provide a mechanism for breaking up broadcast domains. The present invention permits different domains to be assigned to the various user warning and positioning devices, so that said devices may operate in close proximity to each other without interfering with each other's receiving and transmitting functions.

The present invention also provides for adaptive power management. The user warning and positioning device transmits at the lowest possible power level in order to conserve energy, as well as to minimize the risk of enemy detection in military or law enforcement applications. Alternately, the user warning and positioning devices is capable of transmitting at a fairly high power level when operating in challenging environments, such as densely developed urban areas or mountainous environments, or when the user, e.g., a soldier, is laying prone or the asset's vehicle has a low profile. Thus, the present invention's communications module's output power is configurable in a flexible manner by the user warning and positioning device's computer processing means.

In a preferred embodiment of the present invention, the user warning and positioning device's configuration file, encryption key, and/or software is updated using a physical or secure wireless connection from a trusted source. This trust, like the validity of received event warning messages, is based on a digital signature. The present invention's physical connections for updates permit the system to be securely reconfigured when a key or device has been compromised.

Also, the present invention considers the potential exploitation of these devices by adversaries, in the military or law enforcement applications. Given the fact that the user warning and positioning devices are configured to periodically generate and transmit location reports to the network bridges and on to the gateways and/or CCS's, it may be possible for an enemy to triangulate the position of each user warning and positioning device. To address this threat, the user warning and positioning devices' communications module provides the capability to thwart basic triangulation effort by, for example, utilizing spread-spectrum technologies.

Spread-spectrum techniques are methods in which energy generated at a single frequency is deliberately spread over a wide band of frequencies. This is done for a variety of reasons, including increasing resistance to natural interference or jamming and to prevent hostile detection. A contemporary application of this technique is used in the Single Channel Ground and Airborne Radio System (SINCGARS) by changing frequencies (frequency-hopping) several times per second. In a preferred embodiment of the present invention, the user warning and positioning device similarly uses frequency-hopping spread spectrum techniques to thwart possible triangulation efforts.

The system and method of the present invention provide for the integration of the event information and warning notification. Based upon the present invention's exemplary applications, the resulting general method steps can be understood as follows:

Step 1: An action (event) occurs that generates a predictable event(s) that will occur in the future. (Example: An enemy artillery battery shoots at a friendly unit location.)

Step 2: The action (event) is detected by an action detection means, via direct or indirect means, such as, for example, optical, electromagnetic, radio frequency, and/or acoustic methods that discretely or in combination characterize the initial and/or ongoing action. (Example: A friendly artillery locating radar picks up the incoming enemy artillery round and accurately measures its ballistic-based path of flight). Action characterization information is the formulated, and the action characterization information subsequently fed to an event prediction determination process, as described in Step 3.

Step 3: The action characterization information is processed and analyzed in a timely manner. The result of this analysis generates predicted corresponding future event and associated relevant information, defined as an event warning message. The event warning message includes, for example, event type (e.g., enemy attack, approaching severe weather, etc.), predicted location/area impacted by the event, predicted start time of the event, and predicted duration of the event. For example, a command and control system (CCS) associated with friendly artillery locating radar uses the ballistic-based path of flight and speed of the enemy artillery round information received from the friendly artillery locating radar to determine the predicted Time of Impact (PTD) and predicted point of impact (PPI) of the enemy artillery round, with corresponding affected area footprint considering any ballistic measurement errors).

Step 4: The event warning message is universally distributed to all nodes (i.e., all network bridges and all user warning and positioning devices) within the information network without regard to whether a specific node will be affected by the future event. While this so-called "distributed method", which involves communication to all nodes, whether in the affected area or not, exerts increased load on the communications network (e.g., increased use of bandwidth) versus a centralized network configuration (wherein the event warning message is sent only to the network bridge and user warning and positioning devices in the affected area), the distributed network configuration of the present invention provides rapid and accurate event warning/notification to individual nodes, since there are no time delays or asset location errors associated with unit position reporting latencies and centralized computational processes to determine which individual nodes will be specifically impacted by an event. Thus, the present invention permits very short warning/notification time windows between event detection and impact on individual entities. (Example: A CCS generates a set of strike warning messages that are electronically transmitted to all user nodes within the network).

Step 5: Optionally, if either the communications network, information network, and/or versions of components within the system of the present invention are heterogeneous in nature, then a translation of the event warning message may be required in terms of format and content to insure compatibility and continuity of timely transmittal as the event warning message makes its way to the user warning and positioning devices. For example, the CCS generates a variable-message-format (VMF) based strike warning message(s). The unit-borne system addressed for receipt of this strike warning message is only able to parse and understand extensible Markup Language (XML) based messages. An interim system/device/process is required to translate the strike warning message from VMF to XML.)

Step 6: The user warning and positioning devices receive and locally parse/process the future event warning message in a timely manner, via a computer processing means running the user warning device computer program product of the present invention. Whenever an event warning message is received by the user warning and positioning device, the predicted time of the event is compared to the local time to determine whether or not the event will occur at some future time. If it will, the event warning message's authenticity is automatically verified by examining its digital signature. If the signature is valid, the locale that is affected by the future event is automatically compared to the location of the user warning and positioning device. If the user warning and positioning device is within the affected area, it will notify the user, based on the time remaining until the future event, via the sensory notification means. The sensory notification means may include audible alarms, audible spoken warnings and instructions, visual alarms such as flashing lights, and/or vibrations mechanisms.

The user warning and positioning device will also re-transmit the received event warning message to other network bridges and user warning and positioning devices, so that other nodes that may not be in range of the original transmission by the network bridge may also receive the event warning message. All invalid or elapsed event warning messages are logged and then discarded. The re-transmission feature on the user warning and positioning device can be disabled to prolong power life, or to reduce the risk of detection by enemy assets in military and law enforcement applications. (Example: A pager-sized user warning and positioning device carried by an individual dismounted soldier receives and validates an XML-base strike (event) warning message. Computational logic within this device activates several notification mechanisms found within the device, to alert the soldier of an impending enemy strike in his area).

Step 7: Based on the set of alert actions selected by the user for his user warning and positioning device (i.e., the user can select the types of alerts given by his device, according to the situation), the user is warned/notified via one or more sensory means prior to and during the time period of the event occurrence. As discussed above, these sensory indicia include auditory, visual, and/or physical stimulation of an individual's bodily senses. (Example: A pager-sized user warning and positioning device carried by a soldier can be programmed to both vibrate and sound an audible alarm when receiving an event warning message, to notify the affected soldier to change his protective posture prior to impact of an enemy artillery round in his locale).

The present invention's network bridge(s) provides two principle functions. First, it provides an interface between the user warning and positioning devices and the external systems that receive, generate and utilize warning/notification information. In this role, the network bridge translates messages received from other systems into event warning messages. It also translates messages received from the individual user warning and positioning devices into other message formats utilized by other different and multiple command and control systems. Thus, the network bridge also filters messages that should not be sent from one network to the other, e.g., spot reports coming from a terrestrial command and control system.

Second, the network bridge acts as a management device for the individual user warning and positioning devices. The network bridge keeps track of the status of the user warning and positioning devices with which it has communications contact, and permits the selective disablement or remote alteration of any individual user warning and positioning device that appears to have been compromised or lost. The network bridge is capable of configuring and reconfiguring any parameter in the individual user warning and positioning devices, e.g., by changing the URN of a replacement user warning and positioning device issued to a soldier.

The present invention's network bridge communicates with sensor, warning, and command and control systems that use different networks and protocols. For example, the present invention's network bridge can use the internet protocol (IP) at the network layer. Moreover, the network bridge can communicate using both a local area network (LAN) and a point-to-point (PPP) link in order to support both mobile/tactical and fixed installations.

In an embodiment of the present invention, the network bridge device is implemented using a laptop computer running on a conventional operating system. The network bridge supports various formats, such as extensible Markup Language (XML) messages, over an Ethernet interface, Joint Variable Format Message (JVMF) over a point-to-point protocol (PPP) interface, etc. When a command and control system is connected to a tactical network, e.g., SINCGARS, the CCS connects over its serial port to the Inter-Network Controller (INC), which is a tactical router mounted on the radio's vehicular adapter. The serial connection is established using PPP. Then, the CCS queries the INC to determine its configuration and, if necessary, reconfigures it using the simple network management protocol (SNMP). Thereafter, the CCS exchanges regular IP traffic, e.g., event warning messages, across the serial port. When the CCS is running on a LAN, multicast groups are utilized to transmit packets. By contrast, other sensor and warning systems use other languages, such as extensible markup language (XML) for the messages.

The present invention is applicable to numerous CCS's, such as space, airborne, terrestrial and marine-based system. For instance, multiple terrestrial-based systems can be utilized. For example, some CCS's utilize non-persistent transmission control protocol (TCP) connections to send messages. Thus, such CCS's create a client socket that connects to a server socket on the receiving system, i.e., the present system's network bridge, sends the XML message, and then disconnects. On the other hand, other CCS's create a client socket that connects to the server socket on the receiving system, i.e., the network bridge of the present invention, and then maintains that connection indefinitely. When a message needs to be transmitted, there is no delay in setting up a connection and, if the connection is lost, the CCS will immediately detect the lost connection and try to re-establish it.

The present invention permits message and source authentication, encryption, secure reconfiguration of user warning and positioning devices, and remote zero. Accordingly, the system, method and computer program product of the present invention utilize public key infrastructure (PKI) to mitigate security risks to the system itself. According to a preferred embodiment of the present invention, when an individual user warning and positioning device is initially configured, it is loaded with a plurality, e.g., four, separate encryption keys as follows:

1) the device's own certificate;
2) the device's own private key;
3) the certificate of the network bridge serving as the root certificate authority; and
4) the shared secret key for encrypting messages.

Further, keys are issued by the network bridges that are acting as the root certificate authority for all user warning and positioning devices in the network bridge area of operation. Certificates are signed by this root certificate authority (CA) to allow nodes (such as user warning and positioning devices) to authenticate one another. Moreover, certificate revocation is provided. Thus, the present invention permits both a user warning and positioning device, and its associated network bridge, to authenticate each other, and is particularly important whenever the user warning and positioning device's configuration is remotely modified. As a practical field operation protocol, the only key that should be changed over the air is the shared secret key, but only after the identity of the network bridge has been verified.

Moreover, transmission encryption is provided. Accordingly, the encryption key cannot be read out of the radio transceiver module (of the wireless communication means of the user warning and positioning device) by any means. The entire payload of the data packet is encrypted using the key, and the cyclic redundancy check (CRC) is computed across the ciphertext. A module with the wrong key (or no key) will still receive encrypted data, but this data will be unreadable and useless. Likewise, a module with a key will still receive unencrypted data sent from a module without a key, but the output will be similarly meaningless.

According to the present invention, certain types of event warning messages are authenticated upon receipt. Specifically, in these cases the user warning and positioning devices will verify the identity of a message sender when the received message instructs the user warning and positioning device to modify its configuration. Thus, authentication is performed according to the following steps:

Step 1: A network bridge sends a configuration message to a specific user warning and positioning device. This message contains a plurality of values, e.g., three, separated or parsed values as follows:

1) the parameter name, e.g., "retransmit");
2) the desired value, e.g., "no"; and
3) the secure hash of the concatenated parameter name, equality sign, and value, e.g., retransmit=no. This secure hash is a hash, e.g., MD5, of the string encrypted using the bridge's private key.

Step 2: The recipient user warning and positioning device automatically looks in its cache for the sender's (the network bridge mentioned in Step 1) public key. If it doesn't find one, the user warning and positioning device automatically sends a request for this key to the sender. The sender subsequently sends a message with its public key, which has been encrypted using the root certificate authority's private key. The recipient that has the root CA's public key, decrypts the key it received and adds it to its cache.

Step 3: The recipient user warning and positioning device automatically computes the hash, e.g., MD5, of the received string, e.g., retransmit=no. The user warning and positioning device then automatically decrypts the received hash using the sender's public key and compares the received and the computed hash values. If they match, the recipient user warning and positioning device knows that the received configuration message is a legitimate authentic message.

According to the present invention, the event warning message reaches as many user warning and positioning devices as possible, as the event warning message is transmitted to all network bridges and all user warning and positioning devices, even if these network bridges and user warning and positioning devices do not appear to be inside the affected area. In the event that a number of user warning and positioning devices are not in communication contact with a network bridge at a particular point in time, the system of the present invention allows the user warning and positioning devices receiving event warning messages to selectively relay future event warning messages, including multiple occurrences.

The present invention permits retransmission of event warning messages, in appropriate instances, depending on the specified configuration of the user warning and positioning devices, e.g., when the event warning message contains an appropriate configuration file. Thus, a specific event warning message can be transmitted once or multiple times. In the case that the event warning message is to be communicated only once, e.g., to prevent redundancy of an event warning message that has already occurred, the system will ensure that it is configured not to allow retransmissions. The system checks, e.g., a local cache, to ensure that the event warning message has not already been relayed. Conversely, in the case of retransmission, the system checks to ensure that the threatened event has not occurred in the past.

The present invention is also particularly robust through its integration of verbal (as opposed to merely sound) warnings. In particular, specific event warning messages are transmitted to the user warning and positioning device, decoded therein to determine the future event, an appropriate spoken warning broadcast, and a corresponding audible spoken warning made to the user via the sensory notification means of the device, so that users may hear a human voice broadcast by the user warning and positioning device, instructing the user as to what subsequent actions to take in response to the impending event.

The system, method and computer program product of the present invention are also useful for training, simulation, and rehearsal, along with real-time use by organizations such as first responders, public safety, emergency management personnel with warning of harmful events, such as emergency response, homeland security, natural disaster incidents, etc. For example, the present invention may be utilized to support first responders in disaster areas by tracking their location and allowing a command post to send a danger signal (i.e., an event warning message) to the first responders if an unsafe condition is detected in a particular sector. In such case, as the network area is very limited, the danger signal would only affect the personnel in the danger area such as, perhaps, a building about to collapse.

In another example, the present invention may be utilized to support law enforcement officers by allowing a precinct to position the officers to best deter or respond to criminal activity. Further, the present invention may be utilized to provide remotely located individuals, such as skiers, hikers, etc., with warning of harmful events, such as sudden violent weather changes, avalanches, natural disasters, etc. Further, the present invention may be utilized to provide remotely located vehicles, such as watercraft, with advanced warning of impending harmful events in their locale, such as violent ocean conditions, water spouts, sea state changes, tidal waves, etc.

The present invention is applicable to commercial/non-military, as well as military, applications. Further, the possible events addressed by the system, method and computer program product of present invention range from day-to-day events, such as a street-side performance at a large amusement park, road closing due to construction, etc., to life threatening events, such as the imminent collapse of a building within a disaster area, the imminent detonation of a roadside bomb, etc. The human-computer interface implemented at: the user warning and positioning device allows users to reconfigure the settings of the device to determine the content and amount of information that is relayed to user, and can be flexibly configured to address a multitude of events and threats.

Those skilled in the art will recognize that the system, method and computer program product of the present invention has many applications, and that the present invention is not limited to the representative examples disclosed herein. Although illustrative, the embodiments disclosed herein have a wide range of modification, change and substitution that is intended and in some instances some features of the present invention may be employed without a corresponding use of the other features.

Moreover, the scope of the present invention covers conventionally known variations and modifications to the system components described herein, as would be known by those skilled in the art. Accordingly, it is appropriate that the appended claims be construed broadly and in a manner consistent with the scope of the invention.

The invention claimed is:

1. A network event warning system enabling distribution of event warning messages to one or more individual entities within the network information system comprising:
(a) one or more situational awareness workstation and threat warning gateways capable of receiving at least one of event warnings from at least one of linked and remote sensors, and other externally generated event warning messages, each of said situation awareness workstation and threat warning gateways comprising:
a gateway wireless communications means capable of receiving and transmitting data; and
situational awareness workstation computing means in communication with the situational awareness workstation and threat warning gateway and wireless communication means, said situational awareness workstation computing means;
(b) one or more network bridges in communication with the situational awareness workstation and threat warning gateway, each network bridge defining a local node, said network bridges providing a communications interface between individual user warning and positioning devices and the situational awareness workstation and threat warning gateway, each of said network bridges comprising:
(i) a network bridge wireless communications means capable of receiving and transmitting data; and
(ii) network bridge computer processing means in communication with the network bridge and network wireless communications means, individual user warning devices, sensors, and command and control systems;
(c) one or more user warning and positioning devices, each user warning and position device defining an individual node, each of said devices comprising:
(i) a warning device computer processing means;
(ii) a ground positioning system (GPS) means capable of calculating the location of the user warning device;
(iii) a wireless communications means; and
(iv) one or more sensory notification means;
(d) network situational awareness workstation application program code embodied on a computer readable medium for execution on the situational awareness workstation and threat gateway computer processing means capable of authenticating event warning messages, processing and analyzing the event warning messages via an event prediction determination process to produce predicted future event warning messages, and distributing future event warning messages to the network bridges comprising:
(i) application program code operable to decode and authenticate a valid event warning message, input directly or indirectly into the situational awareness workstation and threat warning gateway, by verifying the digital signature of the event warning message;
(ii) application program code operable to input and authenticate event warning message into an event prediction determination process, thereby analyzing the event warning message to predict a corresponding future event with associated relevant information including predicted event type, location, area impacted, start time, and duration;
(iii) application program code operable to distribute the predicted future event and associated relevant information to all network bridges within the information network, without regard to whether a specific local or individual node will be affected by the predicted future event;
(iv) application program code operable to convert the format of the predicted future event information, in terms of electronic format and content, to alternative electronic formats, before distribution;
(e) bridge application program code embodied on a computer readable medium for execution on the network bridge computer processing means for processing event warning messages received from the situational awareness workstation and threat warning gateway, and other external sources, and distributing an authenticated event warning message of an event to occur in the future, said bridge application program code comprising:
- (i) application program code operable to automatically verify the authenticity of event warning messages reporting an event to occur in the future, by examining its digital signature, so as to produce either an invalid or valid event warning message;
- (ii) application program code operable to input a valid event warning message into an event prediction process, wherein the predicted time of the event is compared with the local time, to determine whether the event will occur at some future time;
- (iii) application program code operable to automatically compare the locale to be affected by an authenticated event warning message of an event to occur in the future within the locale of the local node, to determine the affected area;
- (iv) application program code operable to send notification to all user warning and positioning devices within the affected area of an authenticated event warning message of an event predicted to occur in the future;
- (v) application program code operable to relay the event warning message to other local and individual nodes not in the area of the predicted strike warning message;
- (vi) application program code operable to log off and discard all invalid and elapsed event warning messages;
- (vii) application program code operable to input and translate authenticated event warning messages from individual user warning and positioning devices into other message formats utilized by other different command and control systems;
- (viii) application program code operable to filtering event warning messages that should not be sent from one network to the other;
- (ix) application program code operable to track the status of user warning and positioning devices with which the network bridge is in communication with;
- (x) application program code operable to enable the network bridges to communicate with sensors, individual user warning and positioning devices, and command and control systems, using different networks and protocols;
- (xi) application program code operable to issue keys acting as the root certificate authority for all nodes in the network, thereby permitting the network bridges and user warning and positioning devices to authenticate each other;
- (f) user warning and positioning device application program code embodied on a computer-readable medium for execution on the user warning device computer processing means in conjunction with the bridge application program code and the situational awareness workstation program code, said user warning device application program code being capable of decoding messages, validating and analyzing event warning messages, and then issuing a notification of an event predicted to occur in the future in the locale of the user warning device, said user warning device application program code comprising:
  - (i) application program code operable to authenticate event warning messages by verifying the digital signature of the event warning messages;
  - (ii) application program code operable to decoding incoming coded messages;
  - (iii) application program code operable to query a local cache of messages to determine whether an event warning message has already been relayed;
  - (iv) application program code operable to relay event warning messages concerning an event that has not as yet happened and has not as yet been relayed;
  - (v) application program code operable to compare the time of the predicted event to the local time, to determine whether the predicted event will occur at some future time and, if it will, authenticate the message;
  - (vi) application program code operable to compare the locale to be affected by the predicted future event with the locale of the individual node;
  - (vii) application program code operable to notify local nodes within the affected area of the predicted future event, and activating user warning devices based upon the time remaining until the predicted event; and
  - (viii) application program code operable to activate one or more of the sensory notification means in the user warning devices when a valid event warning message is received.

2. The network event warning system of claim 1, wherein the bridge application program code further comprises:
application program code operable to selectively disable or alter individual user warning devices that appear to have been compromised or lost.

3. The network event warning system of claim 1, wherein the bridge application program code further comprises:
application program code operable to reconfigure any parameters in the individual user warning devices and application program code therein.

4. The network event warning system of claim 1, wherein the bridge application program code further comprises:
application program code operable to interface one or more of the network bridges with an optional laptop computer running on an operating system.

5. The network event warning system of claim 1, wherein the bridge application program code further comprises:
application program code operable to revoke the certificate of a user's warning device.

6. The network event warning system of claim 1, wherein the user warning and positioning device application program code further comprises:
application program code operable to convert event warning messages to human voice warnings, said human voice warnings comprising instructions on what subsequent action to take.

7. The network event warning system of claim 1, wherein the user warning and positioning device application program code further comprises:
application program code operable to encrypt outgoing messages.

8. The network event warning system of claim 1, wherein the user warning and positioning device application program code further comprises:
application program code operable to utilize spread-spectrum technology to prevent basic triangulation efforts to locate the user warning and positioning device.

9. The network event warning system of claim 1, wherein the user warning and positioning devices are capable of communicating over wired or wireless systems to the network bridges and other user warning devices.

10. The network event warning system of claim 1, wherein the user warning and positioning device application program code further comprises:

application program code operable to reconfigure the files stored in the user warning device.

11. The network event warning system of claim 1, wherein the bridge application program code further comprises:
application program code operable to connect user warning and positioning devices to command and control systems and sensor systems.

12. A computer program product for tactical distributed event warning over a network event warning system is provided, comprising:
(a) network situational awareness workstation application program code embodied on a computer readable medium for execution on a central computer processing means capable of authenticating received event warning messages, processing and analyzing the event warning messages via an event prediction determination process to produce predicted future event warning messages, and distributing future event warning messages to network bridges comprising:
  (i) application program code operable to decode and authenticate a valid event warning message, input directly or indirectly into the central computer processing means, by verifying the digital signature of the event warning message;
  (ii) application program code operable to input and authenticate event warning messages into an event prediction determination process, thereby analyzing the event warning message to predict a corresponding future event with associated relevant information including predicted event type, location, area impacted, start time, and duration;
  (iii) application program code operable to distribute the predicted future event and associated relevant information to all network bridges within the network, without regard to whether a specific local or individual node will be affected by the predicted future event;
  (iv) application program code operable to convert the format of the predicted future event information, in terms of electronic format and content, to alternative electronic formats, before distribution;
(b) bridge application program code embodied on a computer readable medium for execution on a network bridge computer processing means for processing event warning messages received from the central computer processing means, and other external sources, and distributing an authenticated event warning message of an event to occur in the future, said bridge application program code comprising:
  (i) application program code operable to automatically verify the authenticity of event warning messages reporting an event to occur in the future, by examining its digital signature, so as to produce either an invalid or valid event warning message;
  (ii) application program code operable to input a valid event warning message into an event prediction process, wherein the predicted time of the event is compared with the local time, to determine whether the event will occur at some future time;
  (iii) application program code operable to automatically compare the locale to be affected by an authenticated event warning message of an event to occur in the future within the locale of the local node, to determine the affected area;
  (iv) application program code operable to send notification to all user warning and positioning devices (individual nodes) of an authenticated event warning message of an event predicted to occur in the future;
  (v) application program code operable to relay the event warning message to other local and individual nodes not in the area of the predicted strike warning message;
  (vi) application program code operable to log off and discard all invalid and elapsed event warning messages;
  (vii) application program code operable to input and translate authenticated event warning messages from individual user warning and positioning devices into other message formats utilized by other different command and control systems;
  (viii) application program code operable to filtering event warning messages that should not be sent from one network to the other;
  (ix) application program code operable to track the status of user warning and positioning devices with which the network bridge is in communication with;
  (x) application program code operable to enable the network bridges to communicate with sensors, individual user warning and positioning devices, and command and control systems, using different networks and protocols;
  (xi) application program code operable to issue keys acting as the root certificate authority for all nodes in the network, thereby permitting the network bridges and user warning and positioning devices to authenticate each other;
(c) user warning and positioning device application program code embodied on a computer-readable medium for execution on a user warning device computer processing means in conjunction with the bridge application program code and the situational awareness workstation program code, said user warning device application program code being capable of decoding messages, validating and analyzing event warning messages, and then issuing a notification of an event predicted to occur in the future in the locale of the user warning device, said user warning device application program code comprising:
  (i) application program code operable to authenticate event warning messages by verifying the digital signature of the event warning messages;
  (ii) application program code operable to decoding incoming coded messages;
  (iii) application program code operable to query a local cache of messages to determine whether an event warning message has already been relayed;
  (iv) application program code operable to relay event warning messages concerning an event that has not as yet happened and has not as yet been relayed;
  (v) application program code operable to compare the time of the predicted event to the local time, to determine whether the predicted event will occur at some future time and, if it will, authenticate the message;
  (vi) application program code operable to compare the locale to be affected by the predicted future event with the locale of the individual node;
  (vii) application program code operable to notify local nodes within the affected area of the predicted future event, and activating user warning and positioning devices based upon the time remaining until the predicted event; and (viii) application program code operable to activate one or more sensory notification means in the user warning and positioning devices when a valid event warning message is received.

13. The computer program product of claim 12, wherein the network bridge application program code further comprises:
application program code operable to selectively disable or alter individual user warning and positioning devices that appear to have been compromised or lost.

14. The computer program product of claim 11, wherein the network bridge application program code further comprises:
application program code operable to reconfigure any parameters in the individual user warning and positioning devices and application program code therein.

15. The computer program product of claim 12, wherein the network bridge application program code further comprises:
application program code operable to interface one or more network bridges with an optional laptop computer running on a conventional operating system.

16. The computer program product of claim 12, wherein the network bridge application program code further comprises:
application program code operable to revoke the certificate of a user warning and positioning device.

17. A method for receiving and tactically distributing event warnings is provided, said method comprising the steps of:
(1) electronically receiving an event warning message, having a digital signature, at a situational awareness workstation;
(2) examining the digital signature of the event warning message to authenticate the event warning message;
(3) decoding the authenticated event warning message into a readable format;
(4) analyzing the authenticated event warning message so as to generate corresponding predicted event and associated relevant information, said predicted event and associated relevant information including event type, event location, area impacted, event start time, and event duration, so as to define an event warning message;
(5) converting the event warning message to an electronic format and content readable by a network bridge (local node) and a user warning and positioning device (individual node);
(6) distributing the event warning message by transmission of same from the situational awareness workstation to one or more network bridges, without regard to whether a specific local or individual node will be affected by the predicted event;
(7) receipt of the event warning message in one or more network bridges, and verifying, in the network bridges, the validity of the event warning message received from the situational awareness workstation, so as to authenticate same;
(8) comparing, in the network bridges, the predicted time of the predicted event in the authenticated event warning message with the local time, to determine whether the event has already occurred, and if the predicted event has not occurred, generate a future authenticated event warning message;
(9) filtering out event warning messages, at the network bridges, that should not be sent from one network to another, due to lack of validity or authenticity;
(10) translating the future authenticated event warning messages at the network bridge into other message formats utilized by other different command and control systems and user warning and positioning devices;
(11) issuing, at the network bridges, keys acting as the root certificate authority for all nodes in the network information system, permitting the network bridges and user warning and positioning devices to authenticate each other;
(12) tracking the status of user warning and positioning devices in communication with the network bridge, to determine active or inactive status thereof;
(13) distributing the valid, converted and authenticated event warning message from the network bridges to one or more active user warning and positioning devices;
(14) receiving the valid, converted and authenticated event warning message at the user warning and positioning devices,
(15) examining, in the user warning and positioning devices, the digital signature of the incoming event warning message to verify its authenticity;
(16) discarding all invalid and elapsed warning messages at the user warning and positioning devices;
(17) comparing the locale to be affected by the valid and authenticated event warning message with the locale of the individual node;
(18) comparing in the user warning devices the time of the predicted event or threat in the strike warning message to the local time to determine whether the event will occur at some future time and, if it will, authenticating the message;
(19) decoding, in the user warning and positioning devices, incoming coded event warning messages;
(20) activating one or more notification mechanisms in the user warning and positioning devices, including sensory mechanisms, a user notification concerning the received event warning message.

18. The method for receiving and tactically distributing event warnings of claim 17, further comprising the step of establishing and maintaining communication between the bridge, sensors, user warning devices and command and control systems using different networks and protocols.

19. The method for receiving and tactically distributing event warnings of claim 17, further comprising the following steps:
(21) sending a query from the user warning and positioning devices to a local cache of messages to determine whether the event warning message has already been relayed; and
(22) relaying, from the user warning and positioning devices to other nodes in the network information system, the event warning message concerning an event that has not as yet happened and has not as yet been relayed.

20. The method for receiving and tactically distributing event warnings of claim 17, further comprising converting valid event warning messages to human voice warnings with instructions on what subsequent action to take.

21. The method for receiving and tactically distributing event warnings of claim 17, further comprising sending messages from one or more of the network bridges to one or more of user warning and positioning devices, to either alter, reconfigure, or disable one or more of the user warning and positioning devices.

* * * * *

UNITED STATES PATENT AND TRADEMARK OFFICE
CERTIFICATE OF CORRECTION

PATENT NO. : 7,602,281 B2
APPLICATION NO. : 11/489802
DATED : October 13, 2009
INVENTOR(S) : Manz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 288 days.

Signed and Sealed this

Fifth Day of October, 2010

David J. Kappos
*Director of the United States Patent and Trademark Office*